United States Patent
Wodajo

(10) Patent No.: US 10,492,839 B2
(45) Date of Patent: Dec. 3, 2019

(54) EXPANDABLE OSSEOINTEGRATION BONE FIXATION APPARATUS FOR USE IN A VARIETY OF SETTINGS

(71) Applicant: Felasfa Wodajo, Potomac, MD (US)

(72) Inventor: Felasfa Wodajo, Potomac, MD (US)

(*) Notice: Subject to any disclaimer, the term of this patent is extended or adjusted under 35 U.S.C. 154(b) by 0 days.

(21) Appl. No.: 15/632,668

(22) Filed: Jun. 26, 2017

(65) Prior Publication Data

US 2018/0344366 A1 Dec. 6, 2018

Related U.S. Application Data

(60) Provisional application No. 62/492,270, filed on Apr. 30, 2017.

(51) Int. Cl.
| | |
|---|---|
| A61B 17/72 | (2006.01) |
| A61F 2/46 | (2006.01) |
| A61F 2/00 | (2006.01) |
| A61B 17/80 | (2006.01) |
| A61F 2/28 | (2006.01) |
| A61F 2/30 | (2006.01) |
| A61B 17/68 | (2006.01) |

(52) U.S. Cl.
CPC ...... *A61B 17/7225* (2013.01); *A61B 17/8004* (2013.01); *A61F 2/0077* (2013.01); *A61F 2/28* (2013.01); *A61F 2/30* (2013.01); *A61F 2/4601* (2013.01); *A61B 17/683* (2013.01); *A61B 17/7233* (2013.01); *A61B 17/7241* (2013.01); *A61B 17/7258* (2013.01); *A61B 17/80* (2013.01); *A61F 2002/285* (2013.01); *A61F 2002/2817* (2013.01); *A61F 2002/30405* (2013.01); *A61F 2002/30507* (2013.01); *A61F 2002/30553* (2013.01); *A61F 2002/30579* (2013.01); *A61F 2310/00011* (2013.01)

(58) Field of Classification Search
CPC .......... A61B 17/72–7291; A61B 17/84; A61B 17/844
See application file for complete search history.

(56) References Cited

U.S. PATENT DOCUMENTS 2,051,251 A * 8/1936 Epstein ............... B60B 33/0002
16/38
4,091,806 A * 5/1978 Aginsky ............ A61B 17/7225
606/63

(Continued)

OTHER PUBLICATIONS

Zimmer Biomet Compress product literature, available at https://www.zimmerbiomet.com/medical-professionals/limb-salvage/compress-compliant-pre-stress-device.html prior to Apr. 30, 2017.

*Primary Examiner* — Eduardo C Robert
*Assistant Examiner* — Steven J Cotroneo
(74) *Attorney, Agent, or Firm* — Charney IP Law LLC

(57) ABSTRACT

The embodiments disclosed provide an expandable osseointegration bone fixation apparatus configured to be attached to an affected or fractured bone. The apparatus includes an elongated housing containing a cylindrically shaped intraosseous insert have an expansion mechanism. The insert further includes a set of inwardly angled tapers designed to be attached to a diaphyseal bone where a set of diametrically opposed congruent inserts are configured to incrementally expanded in opposite directions and cause an incremental force against the inside surface of the housing to increase compression to the affected bone.

20 Claims, 5 Drawing Sheets

(56) References Cited

U.S. PATENT DOCUMENTS

| | | | | |
|---|---|---|---|---|
| 4,453,539 A | * | 6/1984 | Raftopoulos | A61B 17/7258 606/63 |
| 4,590,930 A | * | 5/1986 | Kurth | A61B 17/7258 606/63 |
| 4,605,350 A | * | 8/1986 | Chater | F16B 13/0891 411/75 |
| 5,032,130 A | * | 7/1991 | Schelhas | A61F 2/3672 623/22.42 |
| 5,032,133 A | * | 7/1991 | Carbone | A61B 17/7258 623/23.26 |
| 5,116,378 A | * | 5/1992 | Carbone | A61B 17/7258 623/23.26 |
| 5,133,771 A | * | 7/1992 | Duncan | A61F 2/30942 264/DIG. 30 |
| 5,167,666 A | * | 12/1992 | Mattheck | A61B 17/72 606/62 |
| 5,352,228 A | * | 10/1994 | Kummer | A61B 17/1721 606/64 |
| 5,653,763 A | * | 8/1997 | Errico | A61F 2/446 411/55 |
| 6,338,732 B1 | * | 1/2002 | Yang | A61B 17/7216 606/311 |
| 6,383,519 B1 | * | 5/2002 | Sapieszko | C04B 38/0025 424/401 |
| 7,703,727 B2 | * | 4/2010 | Selness | A47B 91/028 248/125.2 |
| 7,799,081 B2 | * | 9/2010 | McKinley | A61F 2/4611 623/17.16 |
| 9,119,635 B2 | | 9/2015 | Booth et al. | |
| 9,155,574 B2 | | 10/2015 | Saravia et al. | |
| 9,314,282 B2 | | 4/2016 | Kecman et al. | |
| 9,314,349 B2 | * | 4/2016 | Greenhalgh | A61F 2/4611 |
| 2003/0065396 A1 | * | 4/2003 | Michelson | A61F 2/30744 623/17.15 |
| 2004/0010313 A1 | * | 1/2004 | Aston | A61L 31/16 623/17.11 |
| 2005/0015154 A1 | * | 1/2005 | Lindsey | A61B 17/68 623/23.46 |
| 2011/0301653 A1 | * | 12/2011 | Reed | A61B 17/1604 606/319 |
| 2016/0361102 A1 | | 12/2016 | Zhang | |

* cited by examiner

EXPANDABLE OSSEOINTEGRATION BONE FIXATION APPARATUS FOR USE IN A VARIETY OF SETTINGS

CROSS-REFERENCE TO RELATED APPLICATION

This application claims the benefit of provisional patent application No. 62/492,270 filed on Apr. 30, 2017 titled "Expandable Osseointegration Bone Fixation Device" by the present inventor.

FIELD

The present embodiment relates to a bone fixation apparatus, and, in particular, to an intramedullary fixation apparatus configured to be durably affixed to an affected bone and enable osseointegration within a plurality of microscopic pores.

BACKGROUND

It is often necessary in orthopedic surgery to affix a metal device into the patient's bone. Typically, surgery such as bone fracture repair uses bone screws to attach metal plates to the bone in order to restrict movement and to ensure the correct positioning of the bones being repaired. However, in other scenarios, the metal device is intended to permanently be incorporated into the patient's skeleton. A common situation is hip or knee joint replacement where the implant is intended to durably adhere to the patient's bones.

Some clinical scenarios, such as patients who have had multiple revision surgeries or bone tumor resections are challenging for current devices, in particular when there is a short segment of bone or only cortical bone is available. In these cases, current fixation technologies provide less than optimal long-term fixation.

Furthermore, currently available devices which are intended for fixation into cortical (shaft) bone require manual impaction of the device to produce pressure between the device and the host bone, which is challenging to reliably reproduce and thus introduces the potential for surgical error. Other devices use a spring-loaded mechanism to produce compression between metal and only the leading edge of the bone. Thus, the osseointegration surface is limited to a small area and so patients are prohibited from bearing weight for many weeks, and even then, the risk of early failure remains high.

This invention is intended to take advantage of the natural tendency of bone to grow into porous metallic surfaces and develop a durable attachment via "osseointegration". This occurs when bone progenitor cells migrate into the metallic pores and form bone within and about the porous structure. This process is well known to allow for durable fixation of metal implants onto bone. Within the scope of the present invention, in each of the below embodiments, the porous and non-porous portions of the device may be coated with proteins from synthetic or animal source such as antibiotics, or include other coatings or radioactive materials to augment the therapeutic options of the invention.

SUMMARY OF THE INVENTION

Embodiments described herein include an expandable osseointegration bone fixation apparatus 100 for use in a variety of settings including orthopedic, craniomaxillofacial and veterinary applications. The apparatus 100 is configured to be affixed to a segment of bone B and allow osseointegration with the affected bone segment. The apparatus is designed to be compressed against both the inside I and the leading edge LE of an affected bone. The apparatus 100 includes a housing 102 containing an insert 104 further comprised of two diametrically opposed congruent sections 106, 108. An expansion bolt 110 at the centerline axis CL produces a sliding motion between the two sections 106, 108 and leads to incremental transition between a first contracted and a second expanded position. The housing 102 includes a first side 112 opposite a second side 114 whose diameters when added together are proportionate to the diameter of the affected bone B. The housing 102 is composed of a metallic material and designed to contain the insert 104 having the two diametrically opposed congruent sections 106, 108 at a trailing end 116 and a set of angled tapers 118 at the leading end 120. The apparatus 102 is compressed against the affected bone B by twisting the expansion bolt 110 causing horizontal expansion of the housing 102 while simultaneously advancing the tapers 118 further into the affected bone. Once inserted, a plurality of microscopic pores along the leading end 120 of the housing 102 and along the outer aspect of the tapers 118 enable osseointegration between the bone B and the several metallic surfaces of the apparatus 100.

In an alternative embodiment, the apparatus 200, 300 includes a plurality of grooves 222, 322 along the exterior walls of the housing portion 202, 302 outside the bone B which enables incremental tightening of a threaded collar 224, 324, causing compression between the collar and the leading edge LE of the bone, in addition to the interior I of the bone.

In a further alternative embodiment, the apparatus includes a collar with a porous surface to slide toward to the affected bone without rotation. An adjustable nut is then applied opposite the sliding collar. When this nut is tightened, it causes increased pressure between the collar and bone, in addition to the pressure between the outside surface of the tapers and the affected bone.

In a further alternative embodiment intended for use near the ends of bones, the apparatus includes a transverse bolt designed to cause expansion of the inserts in a direction perpendicular to longitudinal axis of the bone and a plurality of screws inserted at the leading end of the insert to increase coronal compression of the apparatus against the leading edge of the bone.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

Figure 1A:
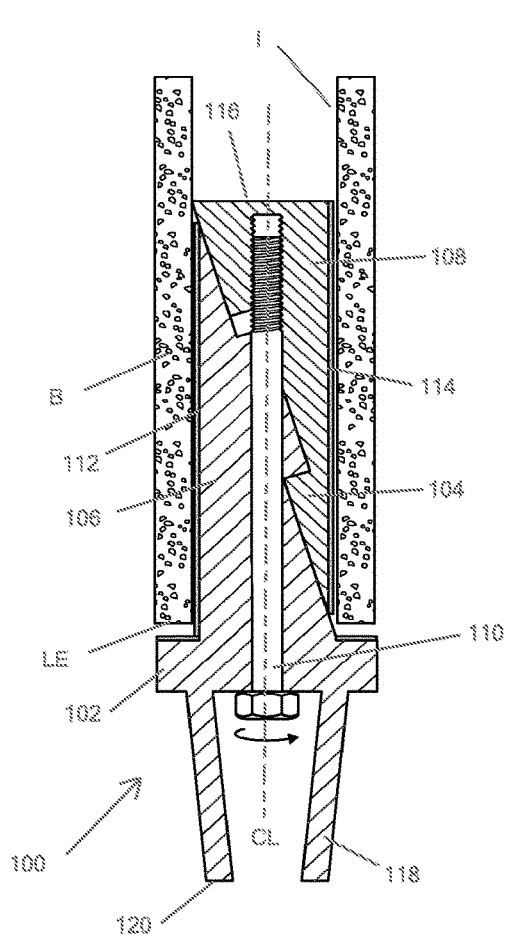
FIG. 1A is a perspective view of an expandable osseointegration bone fixation apparatus, with a tapered conical portion comprising the portion of the housing outside the bone, used to removably attach the apparatus to other metallic components.
Figure 1B:
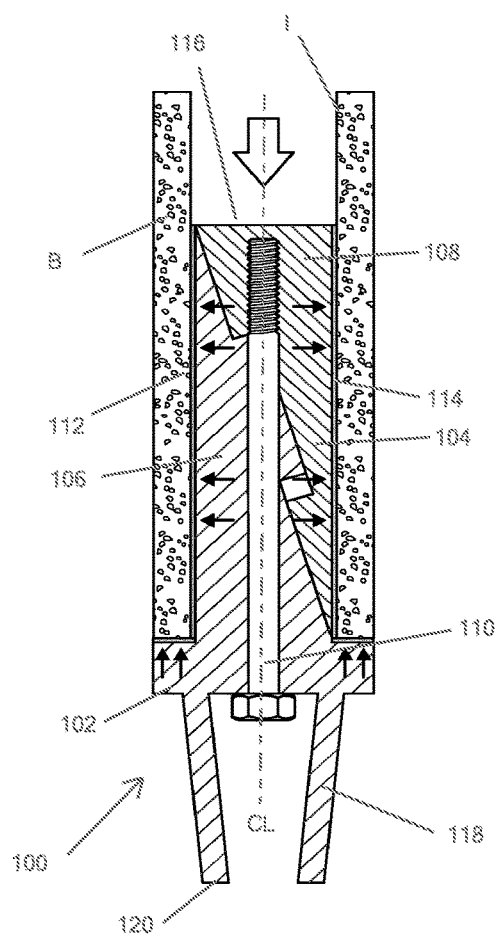
FIG. 1B is a view of the apparatus sliding between the contracted and expanded positions.
Figure 2A:
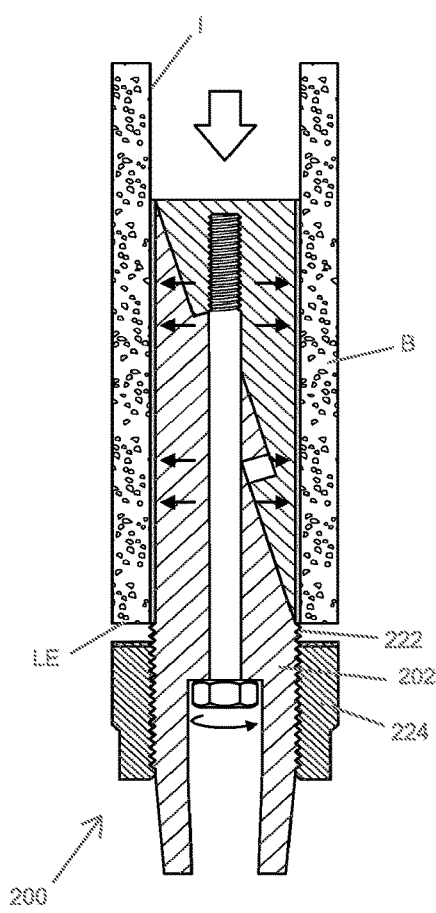
FIG. 2A is an alternate view of the apparatus in an expanded position and further including a threaded collar for additional compression at the end of the bone.
Figure 2B:
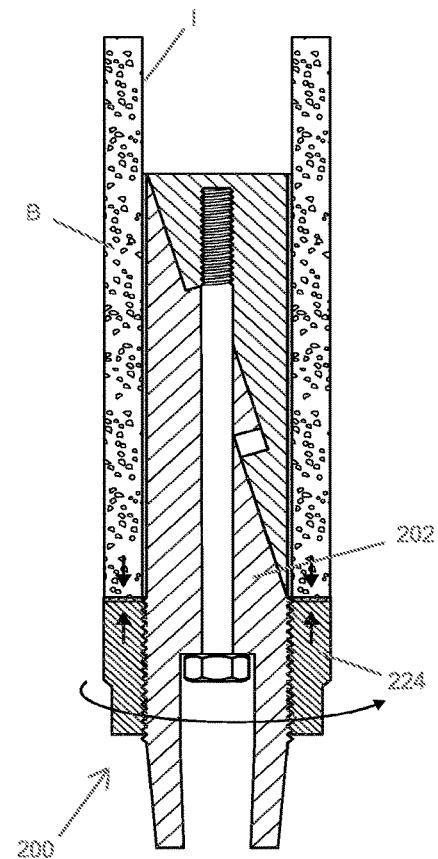
FIG. 2B is the alternate view of apparatus with the threaded collar now compressed against the bone.
Figure 3A:
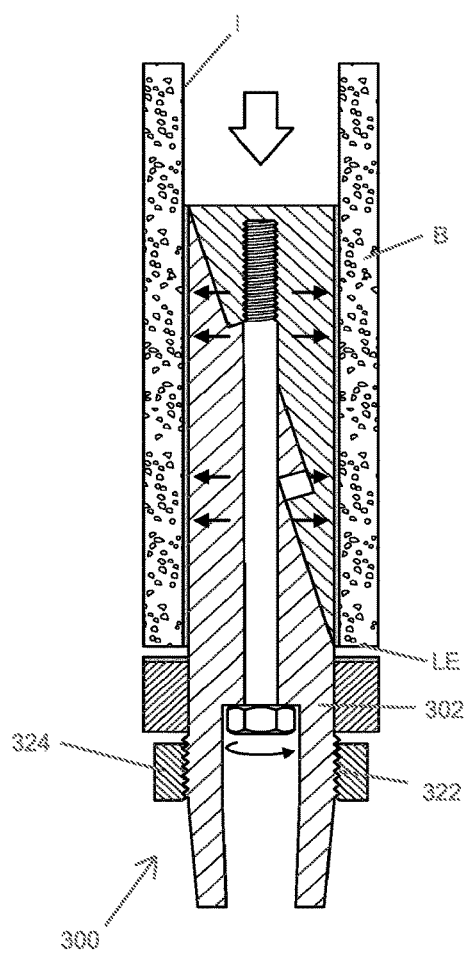
FIG. 3A is a further alternate embodiment of the apparatus with a threaded nut to be used to compress a collar against bone.
Figure 3B:
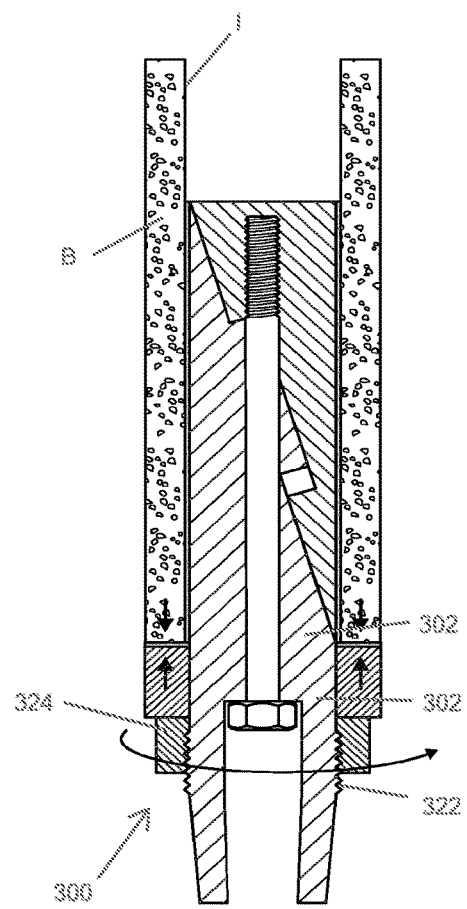
FIG. 3B is a further alternate embodiment now with threaded nut turned to compress collar against bone.
Figure 4:
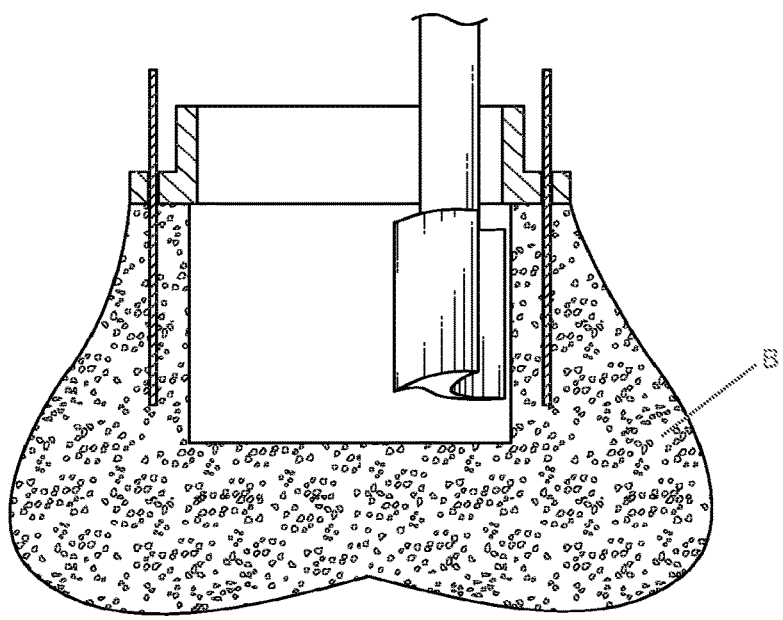
FIG. 4 is a further alternate embodiment of the apparatus intended for use near the end of a bone (metaphysis), demonstrating initial preparation of bone with router and guide.
Figure 5A:
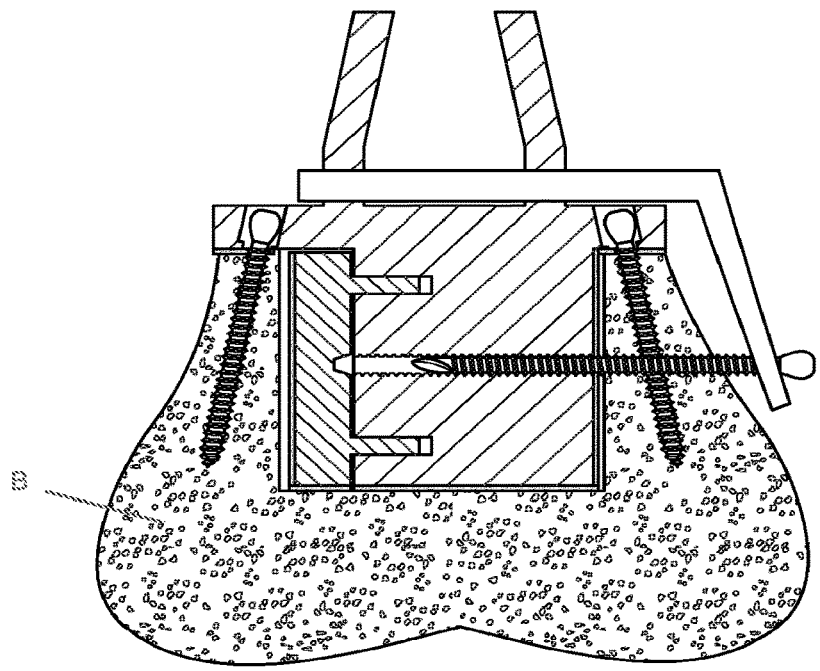
FIG. 5A is the alternate embodiment of the apparatus inserted into the bone, fixed with screws into the bone, internal transverse bolt placed using removable jig.
Figure 5B:
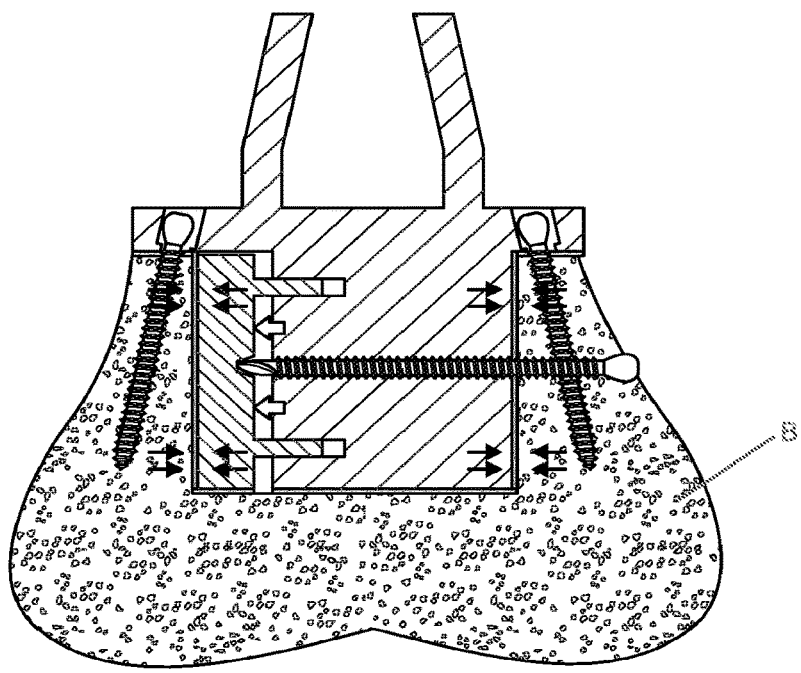
FIG. 5B is the alternate view of the apparatus now with the transverse bolt tightened, causing expansion of the device within the bone.

What is claimed is:

1. An expandable osseointegration cortical shaft bone fixation apparatus, said apparatus comprising:
    a housing having a first section and a second section adjacent to one another, said sections including abutting inside surfaces and outside surfaces, the outside surfaces being adapted to contact the inside of an affected cortical shaft bone, said housing configured to abut a leading edge exterior surface of the affected cortical shaft bone; and
    an insert mechanism configured to be in mechanical connection to the inside surfaces of the first and second sections; the insert mechanism positioned at a centerline axis and adapted to cause the first and second sections to expand in opposite directions to cause an incremental force against the inside of the affected cortical shaft bone when the insert mechanism is transitioned from a first position to a second position;
    said housing further comprising an external compression mechanism adapted to force said housing against the leading edge exterior surface of the affected cortical shaft bone;
    wherein said insert mechanism and said external compression mechanism are capable of being operated independently;
    said apparatus further comprising a connection member for connection to additional surgical components, said connection member comprising a pair of angled tapers, said angled tapers extending inwardly toward each other to a minimum separation distance at an extreme end of said housing.

2. The apparatus of claim 1, wherein the first and second sections of the housing enable lateral movement in a direction perpendicular to the insert mechanism providing circumferential compression between the outside surfaces of the first and second sections of the housing and the inside of the affected cortical shaft bone.

3. The apparatus of claim 2, wherein said connection member is adapted to provide opportunity of connection of the apparatus with other metallic components during surgery.

4. The apparatus of claim 3, wherein an exterior surface of the connection member and a portion of the housing is coated with a layer of materials with therapeutic properties.

5. The apparatus of claim 1, wherein the first and second sections of the housing are comprised of a metallic material having a portion including a plurality of microscopic apertures to enable bone progenitor cells to migrate into the plurality of apertures and promote osseointegration.

6. The apparatus of claim 1, wherein an apparatus width is defined by an inside diameter of the affected cortical shaft bone.

7. The apparatus of claim 1, wherein the insert mechanism includes a plurality of triangular shaped sleeves in mechanical communication and configured to provide longitudinal movement to the insert mechanism when an expansion mechanism is rotated.

8. The apparatus of claim 1, wherein the insert mechanism is cylindrically shaped and includes a threaded portion to increase compression between the housing and the leading edge of the affected cortical shaft bone by allowing a threaded collar to be rotated into position or a separate nut to compress a sliding collar.

9. An expandable osseointegration bone fixation apparatus, comprising:
    a housing with a cylindrically shaped insert contained therein, wherein said housing has a first side opposite a second side and is configured to be affixed within an affected cortical shaft bone and expanded outwardly against an inside surface of the bone when a radial force from said contained insert is applied to an inside surface of the first side and the second side;
    the housing further comprising a surface adapted to apply a compressive force against a leading edge of the affected bone;
    the apparatus further comprising a compression collar rotatably engaged with said housing to provide said compressive force against the leading edge of the affected bone;
    the apparatus further comprising a connection member for connection to additional surgical components, the connection member comprising a pair of angled tapers extending inwardly toward each other to a minimum separation distance at an extreme end of said housing.

10. The apparatus of claim 9, wherein a portion of an outside surface of the metallic housing includes a plurality of microscopic pores to allow progenitor cell migration within the plurality of microscopic pores and promote osseointegration.

11. The apparatus of claim 9, wherein the apparatus further includes a nut at a leading end of the insert, said nut rotatable to cause said radial force.

12. The apparatus of claim 11, wherein said a connection member is adapted to permit connection of said apparatus to further surgical components.

13. A cortical shaft bone fixation apparatus with a porous surface for use in a variety of settings to promote osseointegration, comprising:
    an elongated housing configured to partially fit within a diameter of an affected cortical shaft bone and having first and second sides which move in a manner to provide an outward force to the inside surface of the cortical shaft bone when said first and second sides incrementally transition from a first position to a second position; and an insert further including a bolt along a centerline axis of the insert to provide for each first and second sides to move and increase compression within the diameter of the affected cortical shaft bone;
    the elongated housing further comprising a portion adapted to abut a leading end of the affected cortical shaft bone and provide a force thereon independent of said bolt;
    the apparatus further comprising a connection member for connection to additional surgical components, the connection member comprising a pair of angled tapers extending inwardly toward each other to a minimum separation distance at an extreme end of said elongated housing.

14. The apparatus of claim 13, wherein said connection member extends in a direction along a centerline axis of said bolt.

15. An apparatus adapted for connection to a surgically prepared cortical shaft bone having a leading edge and an interior diameter with a longitudinal centerline, said apparatus comprising:
- a housing having a leading end and a trailing end, said trailing end of said housing comprising an insert portion adapted for placement within an interior diameter of the surgically prepared cortical shaft bone, said insert portion having a first section and second section, said leading end of said housing comprising a surface adapted to abut the leading edge of the surgically prepared cortical shaft bone;
- a first mechanism associated with said housing, said first mechanism adapted to force said first section and said second section of said insert against the interior diameter of the surgically prepared cortical shaft bone;
- said housing further comprising a second mechanism, separate from said first mechanism, and adapted to abut said surface against the leading edge of the surgically prepared cortical shaft bone;
- said first mechanism and said second mechanism being separably operable;
- said apparatus further comprising a member at said leading end of said housing, said member adapted for connection to additional surgical components;
- wherein said member shares a common axis with said insert; wherein said member comprises a pair of angled tapers, said angled tapers extending inwardly toward each other to a minimum separation distance at an extreme leading end of said housing.

16. The apparatus of claim 15, wherein operation of said first mechanism moves said second mechanism toward or away from the leading edge of the surgically prepared cortical shaft bone.

17. The apparatus of claim 16, wherein said first mechanism may not move during operation of said second mechanism.

18. The apparatus of claim 15, wherein said leading end of said housing further comprises external threads, said second mechanism further comprising a collar with internal threads corresponding to said external threads such that said collar may be threaded on said external threads, said collar forming said surface adapted to abut the leading edge of the surgically prepared cortical shaft bone.

19. The apparatus of claim 15, wherein said leading end of said housing further comprises external threads, said second mechanism comprising a sliding collar adapted to extend over said external threads to form said surface adapted to abut the leading edge of the surgically prepared cortical shaft bone and a collar adapted to thread on said external threads.

20. The apparatus of claim 15, wherein said first section and said second section include outside lengths, said first mechanism being adapted to force substantially all of said outside lengths of said first section and said second section against the interior diameter of the surgically prepared cortical shaft bone.

* * * * *